US012576023B2

(12) United States Patent (10) Patent No.: US 12,576,023 B2
Kim et al. (45) Date of Patent: Mar. 17, 2026

(54) FERMENTED NANO-EMULSIFIER COMPOSITION AND PREPARATION METHOD THEREFOR

(71) Applicants:COSMAX AB INC., Seoul (KR); COSMAX, INC., Gyeonggi-do (KR)

(72) Inventors: Kwang Nyeon Kim, Seoul (KR); Ju Hyun Son, Seoul (KR); So Young Park, Seoul (KR); Sa Rang Cho, Seoul (KR); Ju Yun Kim, Seoul (KR); Seok Kyun Yun, Gyeonggi-do (KR); Sugyeong Jeong, Seoul (KR); Seung Hyun Kang, Seoul (KR); Myeong Sam Park, Seoul (KR)

(73) Assignees: COSMAX AB INC., Seoul (KR); COSMAX, INC., Gyeonggi-do (KR)

( * ) Notice: Subject to any disclaimer, the term of this patent is extended or adjusted under 35 U.S.C. 154(b) by 609 days.

(21) Appl. No.: 17/926,162

(22) PCT Filed: May 24, 2021

(86) PCT No.: PCT/KR2021/006398
§ 371 (c)(1),
(2) Date: Nov. 18, 2022

(87) PCT Pub. No.: WO2021/241953
PCT Pub. Date: Dec. 2, 2021

(65) Prior Publication Data
US 2023/0310306 A1 Oct. 5, 2023

(30) Foreign Application Priority Data
May 26, 2020 (KR) ........................ 10-2020-0063024

(51) Int. Cl.
| | |
|---|---|
| *A61K 8/99* | (2017.01) |
| *A61K 8/34* | (2006.01) |
| *A61K 8/64* | (2006.01) |
| *A61K 8/92* | (2006.01) |
| *A61K 8/9728* | (2017.01) |
| *A61Q 19/00* | (2006.01) |

(52) U.S. Cl.
CPC .............. *A61K 8/99* (2013.01); *A61K 8/345* (2013.01); *A61K 8/64* (2013.01); *A61K 8/922* (2013.01); *A61K 8/9728* (2017.08); *A61Q*

*19/00* (2013.01); *A61K 2800/41* (2013.01); *A61K 2800/49* (2013.01); *A61K 2800/85* (2013.01)

(58) Field of Classification Search
CPC ................................................. A61K 2800/413
See application file for complete search history.

(56) References Cited

U.S. PATENT DOCUMENTS

2019/0040475 A1 2/2019 Lee et al.

FOREIGN PATENT DOCUMENTS

| | | | |
|---|---|---|---|
| CN | 109415682 A | 3/2019 | |
| EP | 3476932 A2 | 5/2019 | |
| JP | 5629841 B1 | 11/2014 | |
| KR | 10-2012-0076170 A | 7/2012 | |
| KR | 10-2018-0001459 A | 1/2018 | |
| KR | 10-2018-0001460 A | 1/2018 | |
| KR | 10-1835486 B1 | 3/2018 | |
| KR | 101850421 B1 * | 4/2018 | |
| KR | 10-2019-0033962 A | 4/2019 | |
| KR | 10-2053280 B1 | 12/2019 | |
| WO | WO-2018004224 A2 * | 1/2018 | ............ A61K 35/74 |

OTHER PUBLICATIONS

Office Action from corresponding Chinese Patent Application No. 202180037842.2 dated Oct. 28, 2023. (Google Translation).
International Search Report from corresponding Patent Application No. PCT/KR2021/006398 dated Aug. 30, 2021.

* cited by examiner

*Primary Examiner* — Qiuwen Mi
(74) *Attorney, Agent, or Firm* — Christensen, Fonder, Dardi; Diane E. Bennett; Peter S. Dardi

(57) ABSTRACT

The present invention can provide a method for preparing a fermented nano-emulsifier composition comprising a product obtained by fermenting an oil with a skin flora, and a skin-friendly composition by minimizing the contents of synthetic raw materials according to such a method. Further, it is possible to improve an emulsification power by forming a nano-emulsion in a size of nm, to be adopted to various formulations by enhancing stability of the composition, and to be easily applied to various formulations requiring a function of hypoallergenic skin due to minimization of the skin irritation.

9 Claims, 6 Drawing Sheets

FIG. 8

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. COSMAX CO., LTD.
    46, Ieyakgongdan 2-gil,
    Hyangnam-eup, Hwaseong-si,
    Gyeonggi-do, 18622,
    Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR : *Epidermidibacterium keratini* EPI-7 | Accession number given by the INTERNATIONAL DEPOSITARY AUTHORITY: KCCM11843P |

II. SCIENTIFIC DESCRIPTION AND/OR PROPOSED TAXONOMIC DESIGNATION

The microorganism identified under I above was accompanied by:

☐ a scientific description

☐ a proposed taxonomic designation (Mark with a cross where applicable)

III. RECEIPT AND ACCEPTANCE

This International Depositary Authority accepts the microorganism identified under I above,
which was received by it on June. 08. 2016.  (date of the original deposit)[1]

IV. INTERNATIONAL DEPOSITARY AUTHORITY

| Name : *Korean Culture Center of Microorganisms*<br><br>Address :   Yurim B/D<br>            45, Hongjenae-2ga-gil<br>            Seodaemun-gu<br>            SEOUL 03641<br>            Republic of Korea | Signature(s) of person(s) having the power to represent the International Depositary Authority or of authorized official(s).<br><br>Date. June. 08. 2016 |

[1] Where Rule 6.4(d) applies, such date is the date on which the status of international depositary authority was
acquired; where a deposit made outside the Budapest Treaty after the acquisition of the status of international
depositary authority is converted into a deposit under the Budapest Treaty, such date is the date on which the
microorganism was received by the international depositary authority.

Form BP/4                                                                Sole page (reissue)

FERMENTED NANO-EMULSIFIER COMPOSITION AND PREPARATION METHOD THEREFOR

CROSS REFERENCE TO RELATED APPLICATIONS

This application is a National Stage filing of PCT Application No. PCT/KR2021/006398 filed May 24, 2021, entitled "Fermented Nano-Emulsifier Composition and Preparation Method Therefor", which claims the benefit of priority based on Korean Patent Application No. 2020-0063024 filed on May 26, 2020, and all contents disclosed in the patent application are incorporated as a part of this specification.

TECHNICAL FIELD

The present invention relates to a fermented nano-emulsifier composition comprising a product obtained by fermenting an oil with a skin flora and a method for preparing the same.

BACKGROUND ART

A skin consists of an epidermis, a dermis, and a subcutaneous fat layer. The epidermis is present in the outermost layer of the skin, acts as a protective film for the skin, and is responsible for immune function of the skin. The epidermal layer is mainly composed of keratinocytes, lipid components exist between the keratinocytes, and the outermost layer is composed of proteins.

The human body can be a habitat for various microorganisms, and the microorganisms form a symbiotic relationship with a host and affect the host. A skin flora present in the skin is a microorganism that reproduces on a surface of the skin, and is mainly found in the outermost layer of the epidermis and the upper part (upper layer) of a hair follicle. There are about 1,000 kinds of microorganisms as the skin flora. Among the microorganisms present in the skin, aerobic microorganisms can secrete a lipolytic enzyme that can use a lipid of the epidermal layer.

However, a study on the skin flora and a skin composition using the same are still insufficient.

Accordingly, the present invention is made to provide a fermented nano-emulsifier composition with improved emulsification power by utilizing the skin flora that secretes a lipolytic enzyme, and a method for preparing the same.

DETAILED DESCRIPTION OF THE INVENTION

Technical Problem

A purpose of the present invention is to provide a fermented nano-emulsifier composition from a fermentation product of an oil using a skin flora and a method for preparing the same.

Technical Solution

In order to solve the above problem, the present invention provides a method for preparing a fermented nano-emulsifier composition, comprising the step of:
  preparing a seed culture by culturing the microorganism of accession number KCCM 11843P (Korean Culture Center of Microorganisms (overseas country), Jun. 8, 2016) with a skin flora;

pre-culturing the seed culture to prepare a pre-culture; and
  fermenting the pre-culture to prepare a fermentation product.

According to an embodiment, a medium used in the step of preparing the seed culture may include a R2A (BD Difco, USA) medium.

Further, a medium used in the step of preparing the pre-culture may include a yeast extract, glycerol, casein peptone, a vegetable oil, $K_2HPO_4$, $KH_2PO_4$, $MgSO_4$, and $MgCl_2$.

Furthermore, a medium used in the step of preparing the fermentation product may include a yeast extract, glycerol, casein peptone, a vegetable oil, $K_2HPO_4$, $KH_2PO_4$, $MgSO_4$, and $MgCl_2$.

According to a specific embodiment, the medium used in the step of preparing the seed culture may contain 0.1 to 5 g/L of casein acid hydrolysate, 0.1 to 10 g/L of a yeast extract, 0.1 to 10 g/L of glucose, 0.1 to 5 g/L of a soluble starch, 0.1 to 5 g/L of $K_2HPO_4$, 0.05 to 5 g/L of sodium pyruvate, 0.1 to 5 g/L of casein peptone, and 0.01 to 1 g/L of $MgCl_2$.

Further, the step of preparing the pre-culture may comprise adding 0.1 to 50 g/L of the seed culture to a medium containing 1 to 100 g/L of a yeast extract, 0.1 to 10 g/L of glycerol, 1 to 100 g/L of casein peptone, 10 to 500 g/L of a vegetable oil, 1 to 10 g/L of $K_2HPO_4$, 1 to 10 g/L of $KH_2PO_4$, 1 to 10 g/L of $MgSO_4$, and 0.01 to 3 g/L of $MgCl_2$.

Furthermore, the step of preparing the fermentation product may comprise adding 1 to 300 g/L of the pre-culture to a medium containing 1 to 100 g/L of a yeast extract, 0.1 to 10 g/L of glycerol, 1 to 100 g/L of casein peptone, 10 to 500 g/L of a vegetable oil, 1 to 10 g/L of $K_2HPO_4$, 1 to 10 g/L of $KH_2PO_4$, 1 to 10 g/L of $MgSO_4$, and 0.01 to 3 g/L of $MgCl_2$.

According to an embodiment, the step of preparing the seed culture may comprise culturing the microorganism in an aerobic condition of 15 to 35° C., wherein the culture is terminated at the point of time an absorbance of the spectrophotometer at a wavelength of 600 nm is 0.5.

According to an embodiment, the step of preparing the pre-culture may comprise culturing the seed culture in an aerobic condition of 15 to 35° C., wherein the culture is terminated at the point of time an absorbance of the spectrophotometer at a wavelength of 600 nm is 1.

According to an embodiment, the step of preparing the fermentation product may comprise fermenting the pre-culture for 1 to 10 days at 15 to 35° C.

According to other embodiment of the present invention, there is provided a fermented nano-emulsifier composition prepared by the method as described above.

According to an embodiment, an average particle diameter of the fermented nano-emulsifier may be 100 to 200 nm.

According to another embodiment of the present invention, there is provided a cosmetic composition comprising the fermented nano-emulsifier composition as described above.

Concrete features on the other embodiments of the present invention are shown in the detailed description of the present invention below.

Advantageous Effects

A fermented nano-emulsifier composition using a skin flora according to the present invention can provide a skin-friendly composition by minimizing the contents of synthetic raw materials. In addition, the fermented nano-emulsifier composition makes possible it to improve an emulsification power by forming a nano-emulsion in a size of nm, to be adopted to various formulations by enhancing stability of the composition, and to be easily applied to various formulations having a function of hypoallergenic skin due to minimization of the skin irritation.

BRIEF DESCRIPTION OF THE DRAWINGS

FIG. 8 is a copy of a certificate of deposit of microorganisms, accession number KCCM11843P.

DETAILED DESCRIPTION OF THE EMBODIMENTS

Figure 1:
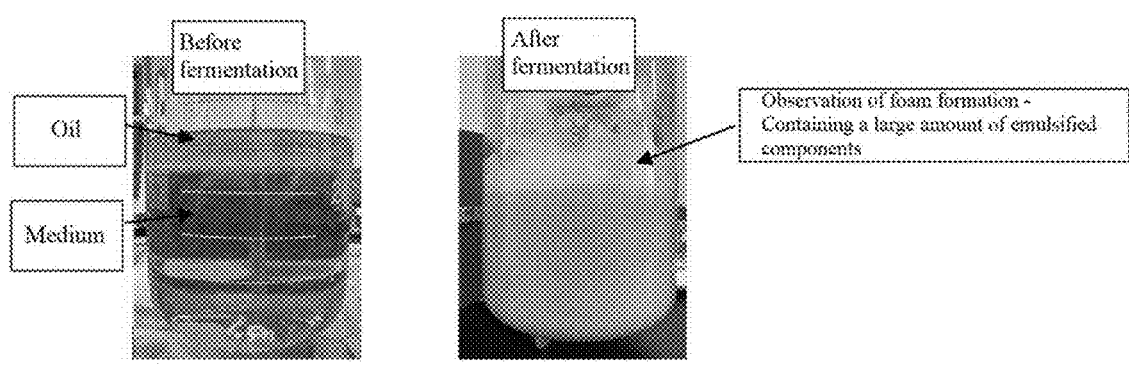
FIG. 1 is a photograph of visually observing the fermentation product according to the present invention.

Since the present invention may apply various modifications and have various embodiments, specific embodiments are intended to be illustrated and described in the specification in detail. However, these descriptions are not intended to limit the present invention to the specific embodiments, but should be understood to include all modifications, equivalents, or substitutions involved in the spirit and scope of the present invention. If it is considered that the detailed descriptions of related known technologies may obscure the gist of the present invention, those descriptions will be omitted.

Hereinafter, a fermented nano-emulsifier composition and a method for preparing the same according to the present invention will be described in detail.

The present invention provides a nano-emulsifier composition with improved emulsification power by using a symbiotic skin flora that has a beneficial effect on a skin, among various microorganisms inhabiting the skin.

Specifically, the present invention provides a method for preparing a fermented nano-emulsifier composition, comprising the step of:

preparing a seed culture by culturing the microorganism of accession number KCCM 11843P (Korean Culture Center of Microorganisms (overseas country), Jun. 8, 2016) with a skin flora;

pre-culturing the seed culture to prepare a pre-culture; and fermenting the pre-culture to prepare a fermentation product.

The skin flora used in the present invention is *Epidermidibacterium keratini* sp. belonging to Sporichthyaceae, as the microorganism of accession number KCCM 11843P (Korean Culture Center of Microorganisms (overseas country), Jun. 8, 2016).

According to an embodiment, a medium used in the step of preparing the seed culture may include a R2A (BD Difco, USA) medium.

Further, a medium used in the step of preparing the pre-culture may include a yeast extract, glycerol, casein peptone, a vegetable oil, $K_2HPO_4$ $KH_2PO_4$, $MgSO_4$, and $MgCl_2$.

Furthermore, a medium used in the step of preparing the fermentation product may include a yeast extract, glycerol, casein peptone, a vegetable oil, $K_2HPO_4$, $KH_2PO_4$, $MgSO_4$, and $MgCl_2$.

According to a specific embodiment, the medium used in the step of preparing the seed culture may contain 0.1 to 5 g/L, for example 0.1 to 1 g/L, of casein acid hydrolysate, 0.1 to 10 g/L, for example 0.1 to 5 g/L, for example 0.1 to 1 g/L, of a yeast extract, 0.1 to 10 g/L, for example 0.1 to 1 g/L, of glucose, 0.1 to 5 g/L, for example 0.1 to 1 g/L, of a soluble starch, 0.1 to 5 g/L, for example 0.1 to 1 g/L, of $K_2HPO_4$, 0.05 to 5 g/L, for example 0.1 to 1 g/L, of sodium pyruvate, 0.1 to 5 g/L, for example 0.1 to 1 g/L, of casein peptone, and 0.01 to 1 g/L, for example 0.01 to 0.1 g/L, of $MgCl_2$.

Further, the step of preparing the pre-culture may comprise adding 0.1 to 50 g/L, for example 1 to 30 g/L, for example 5 to 20 g/L, of the seed culture, to a medium containing 1 to 100 g/L, for example 1 to 50 g/L, of a yeast extract, 0.1 to 10 g/L, for example 0.5 to 5 g/L, of glycerol, 1 to 100 g/L, for example 1 to 50 g/L, for example 1 to 30 g/L, for example 5 to 20 g/L, of casein peptone, 10 to 500 g/L, for example 10 to 300 g/L, for example 10 to 200 g/L, of a vegetable oil, 1 to 10 g/L, for example 3 to 8 g/L, for example 5 to 8 g/L, of $K_2HPO_4$, 1 to 10 g/L, for example 1 to 5 g/L, of $KH_2PO_4$, 1 to 10 g/L, for example 1 to 3 g/L, of $MgSO_4$, and 0.01 to 3 g/L, for example 0.1 to 1 g/L, of $MgCl_2$.

Furthermore, the step of preparing the fermentation product may comprise adding 1 to 300 g/L, for example 50 to 200 g/L, of the pre-culture, to a medium containing 1 to 100 g/L, for example 1 to 50 g/L, of a yeast extract, 0.1 to 10 g/L, for example 0.5 to 5 g/L, of glycerol, 1 to 100 g/L, for example 1 to 50 g/L, for example 1 to 30 g/L, for example 5 to 20 g/L, of casein peptone, 10 to 500 g/L, for example 10 to 300 g/L, for example 10 to 200 g/L, of a vegetable oil, 1 to 10 g/L, for example 3 to 8 g/L, for example 5 to 8 g/L, of $K_2HPO_4$, 1 to 10 g/L, for example 1 to 5 g/L, of $KH_2PO_4$, 1 to 10 g/L, for example 1 to 5 g/L, for example 1 to 3 g/L, of $MgSO_4$, and 0.01 to 3 g/L, for example 0.1 to 1 g/L, of $MgCl_2$.

According to an embodiment, the vegetable oil may include one or more of edible or human body-friendly oils such as a sunflower seed, a grape seed, a canola, a rice seed, an olive, a soybean, an argan, a brown rice, a perilla, a sesame, an almond, a peanut, a corn, a red ginseng, an avocado, a macadamia, a coconut, a rosehip, a vitamin tree seed, a shea fruit, an oil palm, a bergamot fruit, a camellia seed, a safflower seed, an apricot seed, a poppy seed, an evening primrose seed, a castor seed, a green tea seed, a meadowfoam seed, a flax seed, and a hemp, but is not particularly limited to them.

According to an embodiment, the step of preparing the seed culture may comprise culturing the microorganism in an aerobic condition of 15 to 35° C., for example 20 to 30° C., wherein the culture is terminated at the point of time an absorbance of the spectrophotometer at a wavelength of 600 nm is 0.5.

According to an embodiment, the step of preparing the pre-culture may comprise culturing the seed culture in an aerobic condition of 15 to 35° C., for example 20 to 30° C., wherein the culture is terminated at the point of time an absorbance of the spectrophotometer at a wavelength of 600 nm is 1.

According to an embodiment, the step of preparing the fermentation product may comprise fermenting the pre-culture for 24 to 240 hours, for example 72 to 240 hours, for example 120 to 240 hours, at 15 to 35° C., for example 20 to 30° C.

The "fermentation product" may be a culture medium itself obtained by culturing a strain, or a concentrate or lyophilisate thereof. The fermentation product includes a fermented nano-emulsifier.

According to an embodiment, an average particle diameter of the fermented nano-emulsifier according to the present invention may be 100 to 200 nm, for example 150 to 200 nm, for example 160 to 190 nm.

According to another embodiment of the present invention, there is provided a cosmetic composition comprising the fermented nano-emulsifier composition as described above.

The cosmetic composition may comprise ingredients commonly used in the cosmetic composition, such as a stabilizer, a solubilizer, a vitamin, a pigment, a fragrance, an adjuvant, and a carrier.

According to an embodiment, the cosmetic composition of the present invention may be conventionally prepared in the art to which the present invention belongs, and made in any formulation that can be applied dermatologically.

The "dermatologically applicable" may mean that a composition has a relatively non-toxic and harmless effective action to an applied target and is able to contain an external application agent which can be applied to the skin, and further that the composition does not impair the activity and physical properties of the active ingredients while does not cause serious irritation to the applied target without reducing the efficacy of the active ingredients due to a side effect resulting from the composition. The dermatologically applicable cosmetic composition of the present invention includes, for example, a solution, a suspension, an oil solution, an emulsion, a paste, a gel, a pack, a cream, a lotion, a powder, a soap, a surfactant-containing cleansing, an oil, a powder foundation, an emulsion foundation, a wax foundation, a spray and a hair cosmetic, etc., but is not limited thereto.

Specifically, the cosmetic composition can be prepared in the form of the formulations such as a skin lotion, a skin softener, a skin toner, an astringent, a lotion, a gel, a milk lotion, a moisture lotion, a nutritional lotion, a massage cream, a nutritional cream, a moisture cream, a hand cream, a foundation, an essence, an ampoule, a nutritional essence, a pack, a soap, a hair shampoo, a foot shampoo, a cleansing foam, a cleansing lotion, a cleansing cream, a body lotion, and a body cleanser.

Hereinafter, Examples of the present invention will be described in detail so that a person who has an ordinary knowledge in the art can easily carry out the present invention. However, the present invention may be embodied in various different forms and is not limited to the Examples described herein.

Example: Preparation of Fermented Nano-Emulsifier

Seed Culture

The microorganism of accession number KCCM 11843P (Korean Culture Center of Microorganisms (overseas country), Jun. 8, 2016) was seed cultured with a skin flora. The seed culture was prepared by inoculating in a R2A (BD Difco, USA) medium and performing stationary culture under an aerobic condition of 25° C. Specifically, the medium composition consists of casein acid hydrolysate of 0.5 g/L, a yeast extract of 0.5 g/L, a glucose of 0.5 g/L, a soluble starch of 0.5 g/L, $K_2HPO_4$ of 0.3 g/L, sodium pyruvate of 0.3 g/L, casein peptone of 0.5 g/L, and $MgCl_2$ of 0.05 g/L.

The seed culture was terminated at the point of time an absorbance shows 0.5 at a wavelength of 600 nm with a spectrophotometer.

Pre-Culture 10 g/L of the seed culture was added to medium having the composition shown in Tables 1 and 2, and a pre-culture was prepared by performing the culture under an aerobic condition of 25° C. The pre-culture was terminated at the point of time an absorbance was 1.0 at a wavelength of 600 nm with a spectrophotometer.

Fermentation

When a temperature of the medium having the composition shown in Tables 1 and 2 was 25° C., 100 g/L of the pre-culture was added to the medium, and fermentation was performed for 180 hours to prepare fermentation product (culture medium). The fermentation product in which the fermentation was completed using the medium of Example 19 was shown in FIG. 1, and compared with that before the fermentation.

Separation and Purification

The fermentation product was subjected to continuous centrifugation of a high-speed to remove microbial fungi, and the fermentation product from which the fungi were removed was separated into an oil phase and an aqueous phase. The aqueous phase was sequentially sterilized and filtered through a polyethersulfone (PES) membrane filter of 0.45 um and 0.2 um to obtain a fermented nano-emulsifier.

Figure 2:
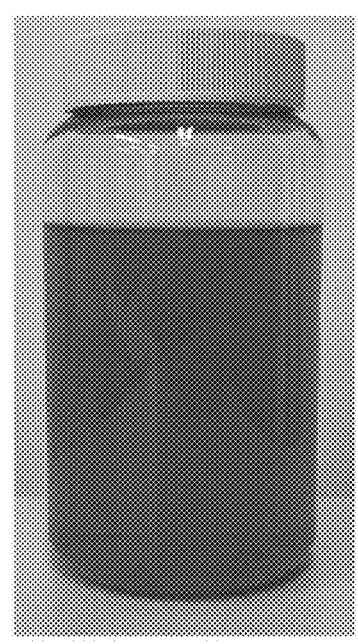
FIG. 2 is a photograph of visually observing the fermented nano-emulsifier obtained after purification.

The fermented nano-emulsifier according to Example 19 was shown in FIG. 2.

TABLE 1

| Classification (g/L) | Example 1 | Example 2 | Example 3 | Example 4 | Example 5 | Example 6 | Example 7 |
|---|---|---|---|---|---|---|---|
| Glycerol | 1 | 5 | 1 | 1 | 1 | 1 | 1 |
| Yeast extract | 1 | 1 | 1 | 10 | 50 | 1 | 10 |
| Casein peptone | 1 | 1 | 10 | 10 | 10 | 20 | 20 |
| Rice seed oil | 10 | 10 | 10 | 50 | 100 | 10 | 50 |
| $K_2HPO_4$ | 7 | 7 | 7 | 7 | 7 | 7 | 7 |
| $KH_2PO_4$ | 3 | 3 | 3 | 3 | 3 | 3 | 3 |
| $MgSO_4$ | 2 | 2 | 2 | 2 | 2 | 2 | 2 |
| $MgCl_2$ | 0.5 | 0.5 | 0.5 | 0.5 | 0.5 | 0.5 | 0.5 |
| Purified water | 974.5 | 970.5 | 965.5 | 916.5 | 826.5 | 955.5 | 906.5 |

TABLE 1-continued

| Classification (g/L) | Example 8 | Example 9 | Example 10 | Example 11 | Example 12 | Example 13 | Example 14 |
|---|---|---|---|---|---|---|---|
| Glycerol | 5 | 1 | 1 | 5 | 1 | 5 | 1 |
| Yeast extract | 10 | 50 | 1 | 1 | 10 | 10 | 50 |
| Casein peptone | 20 | 20 | 50 | 50 | 50 | 50 | 50 |
| Rice seed oil | 50 | 100 | 10 | 10 | 50 | 50 | 100 |
| $K_2HPO_4$ | 7 | 7 | 7 | 7 | 7 | 7 | 7 |
| $KH_2PO_4$ | 3 | 3 | 3 | 3 | 3 | 3 | 3 |
| $MgSO_4$ | 2 | 2 | 2 | 2 | 2 | 2 | 2 |
| $MgCl_2$ | 0.5 | 0.5 | 0.5 | 0.5 | 0.5 | 0.5 | 0.5 |
| Purified water | 902.5 | 816.5 | 925.5 | 921.5 | 876.5 | 872.5 | 786.5 |

TABLE 2

| Classification (g/L) | Example 15 | Example 16 | Example 17 | Example 18 | Example 19 | Example 20 | Example 21 | Example 22 |
|---|---|---|---|---|---|---|---|---|
| Glycerol | 1 | 1 | 1 | 1 | 1 | 1 | 1 | 1 |
| Yeast extract | 1 | 10 | 50 | 1 | 10 | 25 | 50 | 1 |
| Casein peptone | 100 | 100 | 100 | 10 | 10 | 10 | 10 | 20 |
| Rice seed oil | 10 | 50 | 100 | 50 | 100 | 100 | 100 | 50 |
| $K_2HPO_4$ | 7 | 7 | 7 | 7 | 7 | 7 | 7 | 7 |
| $KH_2PO_4$ | 3 | 3 | 3 | 3 | 3 | 3 | 3 | 3 |
| $MgSO_4$ | 2 | 2 | 2 | 2 | 2 | 2 | 2 | 2 |
| $MgCl_2$ | 0.5 | 0.5 | 0.5 | 0.5 | 0.5 | 0.5 | 0.5 | 0.5 |
| Purified water | 875.5 | 826.5 | 736.5 | 925.5 | 866.5 | 851.5 | 826.5 | 915.5 |

| Classification (g/L) | Example 23 | Example 24 | Example 25 | Example 26 | Example 27 | Example 28 | Example 29 |
|---|---|---|---|---|---|---|---|
| Glycerol | 5 | 1 | 1 | 1 | 1 | 1 | 5 |
| Yeast extract | 1 | 50 | 1 | 50 | 1 | 50 | 50 |
| Casein peptone | 20 | 20 | 50 | 50 | 100 | 100 | 100 |
| Rice seed oil | 10 | 100 | 50 | 100 | 50 | 100 | 100 |
| $K_2HPO_4$ | 7 | 7 | 7 | 7 | 7 | 7 | 7 |
| $KH_2PO_4$ | 3 | 3 | 3 | 3 | 3 | 3 | 3 |
| $MgSO_4$ | 2 | 2 | 2 | 2 | 2 | 2 | 2 |
| $MgCl_2$ | 0.5 | 0.5 | 0.5 | 0.5 | 0.5 | 0.5 | 0.5 |
| Purified water | 951.5 | 816.5 | 885.5 | 786.5 | 835.5 | 736.5 | 732.5 |

Experimental Example 1: Evaluation of Optimal Fermentation Condition According to Composition When culturing the strain of KCCM 11843P with a preceding experiment, a turbidity of the culture medium was shown to be higher in the group to which a vegetable oil was added than in the group to which the vegetable oil was not added. Here, the turbidity of the culture medium was measured for an aqueous layer from which the fungi were removed. Therefore, through the preceding experiment, it was determined that the strain of KCCM 11843P would metabolize the vegetable oil as a substrate and also produce an emulsified component. Based on this, it was attempted to find an optimal fermentation condition that could maximize production of the emulsified component by controlling the content of carbon and nitrogen sources in the medium.

For Examples 1 to 29, the optimal fermentation conditions were evaluated by measuring the turbidity of the culture medium and the number of the microbial fungi. The seed culture was carried out in the above method, and the pre-culture was performed with the composition shown in each of the Examples, and the same composition was evaluated after fermentation at 25° C. and 200 rpm for 140 hours.

The method for measuring the turbidity of the culture medium is as follows. The culture medium was centrifuged at 3,088 g for 15 minutes to remove the microbial fungi, and the culture medium from which the microbial fungi were removed was separated into an oil layer and an aqueous layer. The aqueous layer was sequentially sterilized and filtered through a polyethersulfone (PES) membrane filter of 0.45 um and 0.2 um. It was observed that a nano-emulsion having a size of 0.2 um or less was dispersed in the culture medium from which the fungi were removed by the above method. The higher the content of the emulsified component, the higher the density of the formed nano-emulsion, so it was determined that it could be compared with the turbidity. Therefore, the aqueous layer from which the fungi were removed after fermentation was diluted 10-fold with a purified water, and filtered through the membrane filter of 0.2 um to measure an absorbance at a wavelength of 600 nm, the results of which were shown in Table 3. A spectrophotometer (BIO Teck, Korea) was used as the measurement device.

In addition, an amount of the fungi in the culture medium was measured. After taking the culture medium for each of the Examples and centrifuging it at 13,000 g for 30 minutes, a supernatant was discarded and only the microbial fungi were obtained. After washing them once in 0.85% NaCl, they were suspended in 0.85% NaCl of the same volume as the culture medium, and diluted 10-fold with the purified water to measure an absorbance at a wavelength of 600 nm, the results of which were shown in Table 3. A spectrophotometer (BIO Teck, Korea) was used as the measurement device.

TABLE 3

| Classification | O.D 600 nm | |
| | Turbidity of culture medium | Amount of fungi |
| --- | --- | --- |
| Example 1 | 0.623 | 0.203 |
| Example 2 | 0.415 | 0.499 |
| Example 3 | 0.644 | 0.156 |
| Example 4 | 0.691 | 0.198 |
| Example 5 | 0.112 | 0.885 |
| Example 6 | 0.421 | 0.123 |
| Example 7 | 0.495 | 0.452 |
| Example 8 | 0.306 | 0.594 |
| Example 9 | 0.131 | 0.799 |
| Example 10 | 0.173 | 0.303 |
| Example 11 | 0.200 | 0.464 |
| Example 12 | 0.403 | 0.379 |
| Example 13 | 0.397 | 0.577 |
| Example 14 | 0.162 | 0.851 |
| Example 15 | 0.241 | 0.569 |
| Example 16 | 0.192 | 0.675 |
| Example 17 | 0.098 | 0.735 |
| Example 18 | 0.611 | 0.205 |
| Example 19 | 0.802 | 0.248 |
| Example 20 | 0.590 | 0.674 |
| Example 21 | 0.127 | 0.819 |
| Example 22 | 0.654 | 0.318 |
| Example 23 | 0.206 | 0.502 |
| Example 24 | 0.251 | 0.603 |
| Example 25 | 0.653 | 0.109 |
| Example 26 | 0.160 | 0.574 |
| Example 27 | 0.100 | 0.451 |
| Example 28 | 0.143 | 0.500 |
| Example 29 | 0.080 | 0.901 |

As a result of the experiment, an amount of the fungi in Example 19 was measured at a level lower than the average of each of the Examples, whereas the turbidity of the culture medium from which the fungi were removed was measured to be the highest. It can be determined that a degree of emulsification in the oil added to the culture medium by microorganisms is optimal and contains the most emulsified components. Therefore, Example 19 was selected as the optimal fermentation condition.

Experimental Example 2: Evaluation of Production of Emulsified Component by Skin Flora In order to compare and evaluate production of emulsified components depending on types of fungi, the representative skin flora, *Acinetobacter calcoaceticus, Staphylococcus epidermidis, Staphylococcus aureus, Cutibacterium acnes*, and *Sporichthya* spp. which is closely related to KCCM 11843P were cultured and compared with the strain of KCCM 11843P. The evaluation was performed in the same method as that of Experimental Example 1, and the fermentation was carried out on the same composition as that of Example 19. The results were shown in Table 4.

TABLE 4

| Classification | Inoculated strain | Turbidity of culture medium | Amount of fungi |
| --- | --- | --- | --- |
| Example 19 | KCCM 11843P | 0.802 | 0.248 |
| Comparative Example 1 | *A. calcoaceticus* | 0.427 | 0.184 |
| Comparative Example 2 | *S. epidermidis* | 0.200 | 0.093 |
| Comparative Example 3 | *S. aureus* | 0.014 | 0.047 |
| Comparative Example 4 | *C. acnes* | 0.343 | 0.200 |
| Comparative Example 5 | *Sporichthya* spp. | 0.230 | 0.122 |

As a result of the experiment, it could be confirmed that the KCCM 11843P strain produced the most emulsified component.

Further, since Comparative Examples 2 and 4 had the foulest odor in the culture medium, it was determined that the culture medium itself was difficult to apply to a cosmetic composition.

On the other hand, it was determined that the culture medium of Example 19 was close to odorless and easy to use as the cosmetic composition.

Experimental Example 3: Confirmation of Optimal Fermentation Time of Example 19

Through Experimental Example 1, it was confirmed that Example 19 is under the condition of the optimal pre-culture medium and fermentation medium. An Experiment for determining the point of time secondary metabolites of microorganisms are generated and fermentation is terminated was conducted by measuring a pH, an amount of the fungi, and a turbidity of the culture medium during the culturing period.

The change in pH can confirm a degree of production of the metabolites in the course of fermenting the microorganisms. Specifically, after the culture medium sampled by time was centrifuged at 3,088 g for 5 minutes, an aqueous layer except for fungi and an oil layer was taken and measured with a pH meter (Mettler toledo, FP20).

As a result of evaluating every time, the pH showed a tendency to rise from the initial pH 6.6 to pH 8.3 through a total of two steps and to be constant thereafter. This was shown in FIG. 3.

It was found that the change in pH tended to increase depending on production of the secondary metabolites of the microorganisms, and the metabolites were produced in the stagnant phase after the logarithmic phase during the microbial growth phase. According to FIG. 3, as the pH starts to rise again before and after 80 hours of the fermentation, the turbidity also increases rapidly. This period corresponds to the stagnant phase from the late logarithmic phase during the microbial growth phase, so it can be seen that the secondary metabolism of the microorganisms occurs.

Therefore, the turbidity of the culture medium was increased by the secondary metabolites of the microorganisms, and it can be expected that this is a kind of the emulsifier component.

The point of time the turbidity of the culture medium from which the fungi were removed no longer increased after the secondary metabolism of the microorganisms occurred was considered to be the point of time the emulsified components were maximally generated, and this was judged as an end point of the fermentation. According to FIG. 3, after 180 hours of the fermentation, the turbidity of the culture medium from which the fungi were removed showed a tendency to be constant without increase thereof. Therefore, before and after 180 hours was determined as the end point of the fermentation.

Experimental Example 4: Analysis of Particle Size

Figure 4:
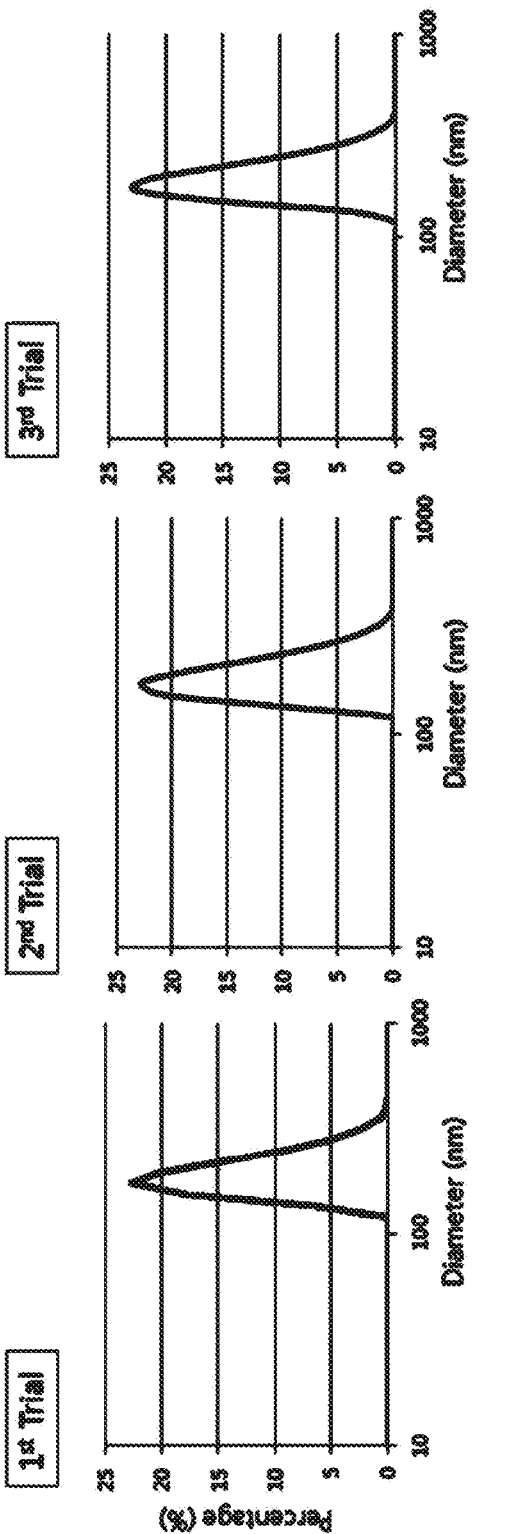
FIG. 4 is graphs showing analysis results of the particle sizes.

For measuring the particle size, the fermented nano-emulsifier according to Example 19 was diluted 10-fold with a purified water, and then the sample was analyzed. A particle size analyzer (HORIBA Scientific, Japan) was used as the measurement device. The results were shown in FIG. 4, and an average particle diameter was measured to be about 181.7 nm.

Experimental Example 5: Observation of Nano-Emulsion

The nano-emulsion formed in the fermented nano-emulsifier, which was obtained by separating and purifying the culture medium according to Example 19, was observed with a transmission electron microscope (JEM-F200, JEOL).

The sample was pretreated by dropping a drop on a Cu grid coated with a carbon and drying it at a room temperature for 6 hours, and observed with a microscope.

Figure 5:
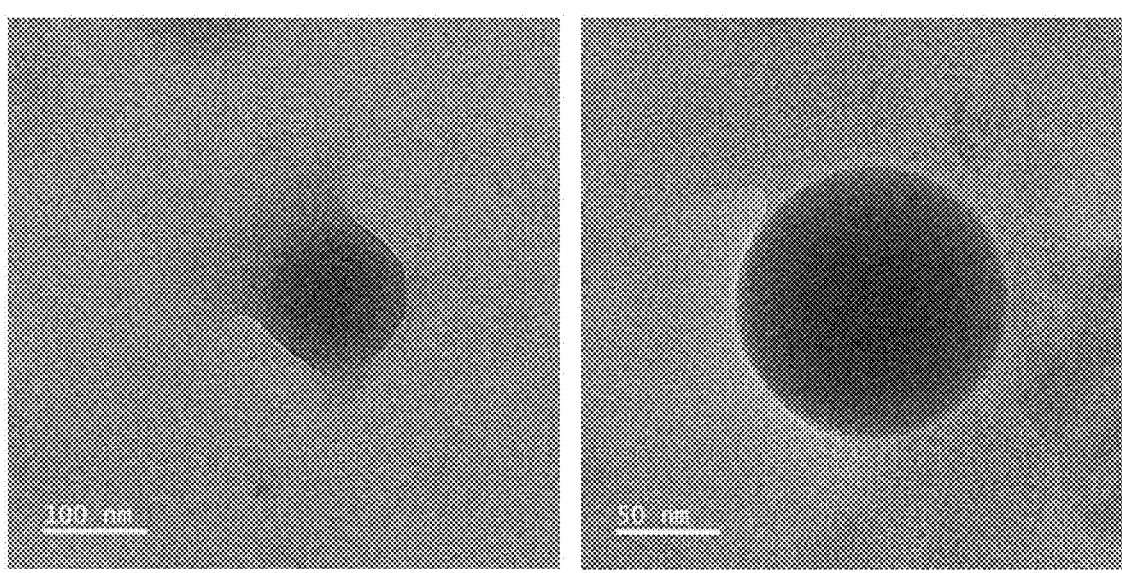
FIG. 5 is photographs of observing a nano-emulsion of the fermented nano-emulsifier with a transmission electron microscope.

The micrograph was shown in FIG. 5. It can be seen that a round-shaped nano-emulsion (micelle) is formed.

Experimental Example 6: TLC Analysis

The fermented nano-emulsifier according to Example 19 was analyzed by a TLC (Thin Layer Chromatography) for production of the emulsified component under the culture condition and for quantitative comparison.

1N HCl was added to the obtained a fermentation broth to adjust a pH to 2-3. An organic solvent mixed with chloroform and methanol in a ratio of 2:1 (v/v) was added to the fermentation broth in a ratio of 2:1 (v/v) and stirred at 25° C. for 2 hours, followed by allowing to stand overnight. Then, the emulsified component was transferred to a lower layer solution (chloroform) for purification. The obtained chloroform was concentrated and volatilized under a reduced pressure, and the remaining emulsified component was dissolved in chloroform.

Figure 6:
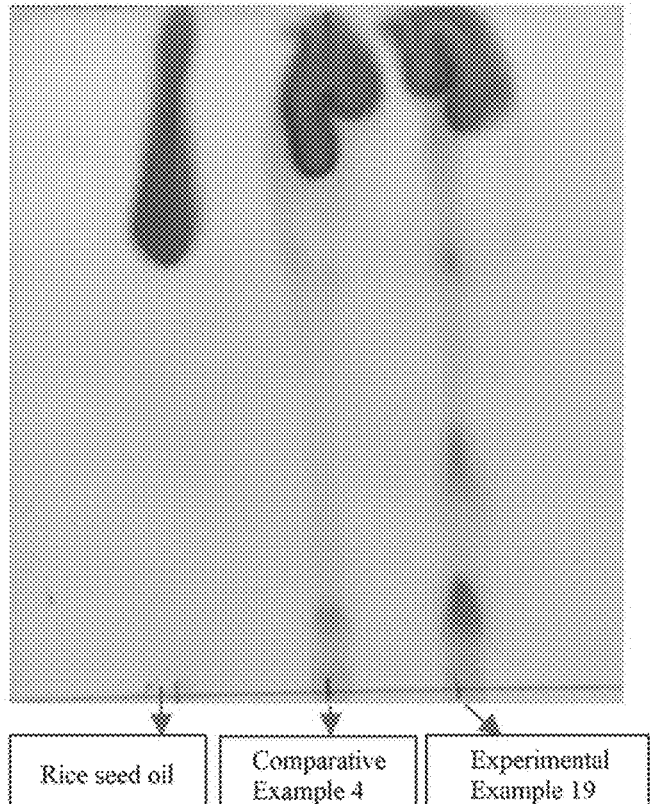
FIG. 6 is a chromatogram showing a TLC analysis result.

The purified product (emulsified component) was dripped onto a silica gel TLC plate (TLC Silica gel 60, Merck; 5 cm×6.5 cm), and was developed to the end point with a mobile phase containing chloroform, methanol and acetic acid (6.5:2:0.2 v/v). After 10% sulfuric acid mixed with ethanol was sprayed and dried on a naturally-dried plate, the plate was heated at 100° C. for 5 minutes to visualize spots. As a result, the spots of polar lipids could be observed, as shown in FIG. 6.

20% of a rice seed oil dissolved in chloroform was used as a comparison group. Compared with the purified product of Comparative Example 4, more diverse and large amounts of the polar lipids were observed in the purified product of Example 19.

Experimental Example 7: Degree of Emulsion Layer Formation by Fermentation Period As the fermentation according to Example 19 proceeded, it was attempted to confirm a time when an actual emulsion layer was formed. For each fermentation period, 10 ml of the culture medium was taken and observed after centrifugation at 3,088 g for 5 minutes.

Figure 7:
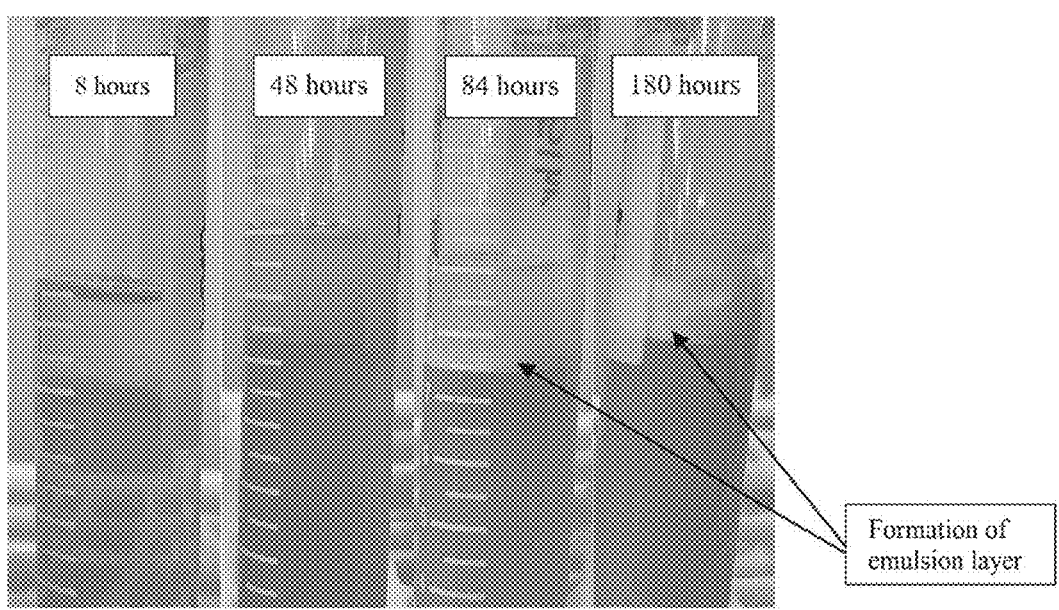
FIG. 7 is photographs of visually observing formation of an emulsion layer by fermentation time.

As a result of the experiment, it was confirmed that the emulsion layer was formed between the oil layer and the aqueous layer before and after 84 hours of the fermentation, which was shown in FIG. 7.

Figure 3:
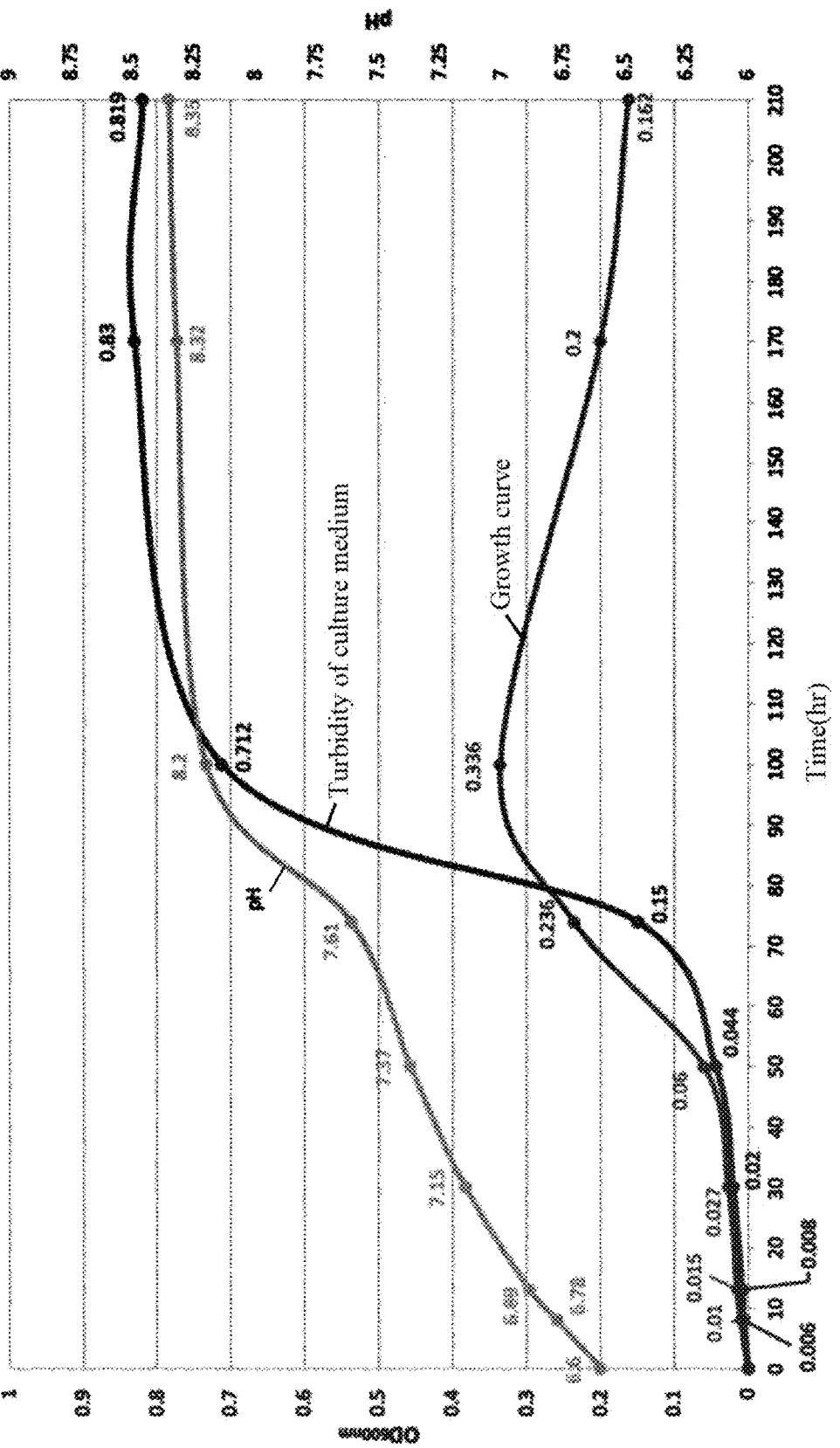
FIG. 3 is a graph measuring growth curve, turbidity of the culture medium, and change in pH under the optimal fermentation condition.

Compared with FIG. 3, the emulsion layer is formed at a time very similar to the time when the secondary metabolism begins to occur. Through this, it can be seen that an emulsified component is formed as the secondary metabolite.

Experimental Example 8: Evaluation of Skin Irritation

For the fermented nano-emulsifier separated and purified according to Example 19 of the present invention, evaluation of a primary skin irritation was performed to see whether or not the skin irritation occurred. The evaluation agency was commissioned by Corederm Co., Ltd. Thirty-two subjects were selected and applied on their back sites for 24 hours, and then at 30 minutes, 24 hours and 48 hours after the application was removed, the dermatologist evaluated the presence or absence of the primary skin irritation, respectively. The evaluation of the skin irritation was based on the standards of the International Contact Dermatitis Research Group (ICDRG) and the Personal Care Products Council (PCPC), which is American Cosmetics Association, and the results were shown in Table 5.

TABLE 5

| | Experimental Material | | | |
| | 30 mins after application (48 hr) | | 24 hrs. after application (72 hr) | |
| Nos. of subjects to be evaluated | 1 | 2 (N.C) | 1 | 2 (N.C) |
|---|---|---|---|---|
| 1 | — | — | — | — |
| 2 | — | — | — | — |
| 3 | — | — | — | — |
| 4 | — | — | — | — |
| 5 | — | — | — | — |
| 6 | — | — | — | — |
| 7 | — | — | — | — |
| 8 | — | — | — | — |
| 9 | — | — | — | — |
| 10 | — | — | — | — |
| 11 | — | — | — | — |
| 12 | — | — | — | — |
| 13 | — | — | — | — |
| 14 | — | — | — | — |
| 15 | — | — | — | — |
| 16 | — | — | — | — |
| 17 | — | — | — | — |
| 18 | — | — | — | — |
| 19 | — | — | — | — |
| 20 | — | — | — | — |
| 21 | — | — | — | — |
| 22 | — | — | — | — |
| 23 | — | — | — | — |
| 24 | — | — | — | — |
| 25 | — | — | — | — |
| 26 | — | — | — | — |
| 27 | — | — | — | — |
| 28 | — | — | — | — |
| 29 | — | — | — | — |
| 30 | — | — | — | — |
| 31 | — | — | — | — |
| 32 | — | — | — | — |

Example 30: Preparation of Essence Formulation

An essence formulation containing the fermented nano-emulsifier separated and purified according to Example 19 was prepared according to the composition of the table below. Specifically, the raw material Nos. 2 to 7 were sequentially added to the raw material No. 1 in the table below, and dissolved by stirring. Afterwards, the raw material Nos. 8 to 9 were sequentially added to a reaction vessel containing the raw material Nos. 1 to 7, and uniformly dissolved and mixed to complete the essence formulation.

TABLE 6

| Classification | Raw material | weight (%) |
|---|---|---|
| 1 | Example 19 | 74.22 |
| 2 | Carbomer | 0.1 |
| 3 | Dipropylene glycol | 8.0 |
| 4 | Glycerin | 5.0 |
| 5 | Butylene glycol | 10.0 |
| 6 | 1,2 Hexanediol | 1.5 |
| 7 | Xanthan gum | 0.08 |
| 8 | Tromethamine | 0.1 |
| 9 | Hyaluronic acid (1%) | 1.0 |
| | Total | 100 |

Example 31: Preparation of Skin Formulation

A skin formulation containing the fermented nano-emulsifier separated and purified according to Example 19 was prepared according to the composition of the table below. Specifically, the raw material Nos. 2 to 7 were sequentially added to the raw material No. 1 in the table below, and uniformly dissolved and mixed to produce the skin formulation.

TABLE 7

| Classification | Raw material | Weight (%) |
|---|---|---|
| 1 | Example 19 | 85.92 |
| 2 | Glycerin | 3.0 |
| 3 | Butylene glycol | 7.0 |
| 4 | 1,2 Hexanediol | 1.5 |
| 5 | Xanthan gum | 0.08 |
| 6 | Glycereth-26 | 2.0 |
| 7 | Hyaluronic acid (1%) | 0.5 |
| | Total | 100 |

Experimental Example 9: Evaluation of Stability

The stability of the essence formulation according to Example 30 and the stability of the skin formulation according to Example 31 was evaluated under a certain storage temperature condition. Each of the formulations was stored for 3 months at a room temperature and 25° C. under a normal condition, and stored for 1 month at a low temperature (−5° C.) and a high temperature (50° C.) with circulation (−5 to 40° C./12 hr) under a severe condition. Then, the pH and separability appearance for each of the formulations were observed. Change in the formulations was observed after 3 months under the normal condition, and observed after 1 month under the severe condition. The results were shown in Tables 8 and 9.

TABLE 8

| Normal condition | | Essence formulation | Skin formulation |
|---|---|---|---|
| Room temperature 25° C. | pH | No change | No change |
| | Separability | No change | No change |
| | pH | No change | No change |
| | Separability | No change | No change |

TABLE 9

| Severe condition | |
|---|---|
| −5° C. | pH |
| | Separability |
| 50° C. | pH |
| | Separability |
| Circulation (−5~40° C./12 hr) | pH |
| | Separability |

From the above result, it was confirmed that the formulations of Examples 30 and 31 had no change in the pH and the separation appearance according to the storage conditions. This substantiates that, by adding the fermented nano-emulsifier of Example 20, an emulsion can be formed on the composition even without using a synthetic surfactant and a high-pressure device, thereby producing a stable and convenient cosmetic formulation. Through this, it is possible to prepare the formulation that is safer for the skin by minimizing synthetic chemical cosmetic components.

As described above, it was confirmed by the present invention that the skin flora can form a fermented nano-emulsifier by using an oil. It was further confirmed that the fermented nano-emulsifier according to the present invention makes possible it to improve an emulsification power even without the use of a chemical surfactant by forming a nano-emulsion in a size of nanometer (nm), to be adopted to various formulations by enhancing stability of the composition, and to minimization of the skin irritation.

In the above, a specific part of the present invention has been described in detail, and therefore, any person who has an ordinary knowledge in the art will be able to fully appreciate that these specific descriptions are only preferred embodiments, and accordingly, the scope of the present invention is not limited by the specific embodiments described above.

What is claimed is:

1. A method for preparing a fermented nano-emulsifier composition, comprising the step of:

preparing a seed culture by culturing the microorganism of accession number KCCM 11843P (Korean Culture Center of Microorganisms (overseas country), Jun. 8, 2016) with a skin flora;

pre-culturing the seed culture to prepare a pre-culture; and fermenting the pre-culture to prepare a fermentation product comprising a fermented nano-emulsifier, wherein a medium used in the step of preparing the fermentation product includes a yeast extract, glycerol, casein peptone, a vegetable oil, $K_2HPO_4$, $KH_2PO_4$, $MgSO_4$, and $MgCl_2$.

2. The method according to claim 1, wherein a medium used in the step of preparing the seed culture comprises casein acid hydrolysate, a yeast extract, a glucose, a soluble starch, $K_2HPO_4$, sodium pyruvate, casein peptone, and $MgCl_2$.

3. The method according to claim 1,
wherein a medium used in the step of preparing the pre-culture includes a yeast extract, glycerol, casein peptone, a vegetable oil, $K_2HPO_4$, $KH_2PO_4$, $MgSO_4$, and $MgCl_2$.

4. The method according to claim 1,
wherein the medium used in the step of preparing the seed culture contains 0.1 to 5 g/L of casein acid hydrolysate, 0.1 to 10 g/L of a yeast extract, 0.1 to 10 g/L of glucose, 0.1 to 5 g/L of a soluble starch, 0.1 to 5 g/L of $K_2HPO_4$, 0.05 to 5 g/L of sodium pyruvate, 0.1 to 5 g/L of casein peptone, and 0.01 to 1 g/L of $MgCl_2$.

5. The method according to claim 1,
wherein the step of preparing the pre-culture comprises adding 0.1 to 50 g/L of the seed culture to a medium containing 1 to 100 g/L of a yeast extract, 0.1 to 10 g/L of glycerol, 1 to 100 g/L of casein peptone, 10 to 500 g/L of a vegetable oil, 1 to 10 g/L of $K_2HPO_4$, 1 to 10 g/L of $KH_2PO_4$, 1 to 10 g/L of $MgSO_4$, and 0.01 to 3 g/L of $MgCl_2$.

6. The method according to claim 1,
wherein the step of preparing the fermentation product comprises adding 1 to 300 g/L of the pre-culture to the medium used in the step of preparing the fermentation product, wherein the medium comprises 1 to 100 g/L of a yeast extract, 0.1 to 10 g/L of glycerol, 1 to 100 g/L of casein peptone, 10 to 500 g/L of a vegetable oil, 1 to 10 g/L of $K_2HPO_4$, 1 to 10 g/L of $KH_2PO_4$, 1 to 10 g/L of $MgSO_4$, and 0.01 to 3 g/L of $MgCl_2$.

7. The method according to claim 1,
wherein the step of preparing the seed culture comprises culturing the microorganism in an aerobic condition of 15 to 35° C., and the culture is terminated at the point of time an absorbance of the spectrophotometer at a wavelength of 600 nm is 0.5.

8. The method according to claim 1,
wherein the step of preparing the pre-culture comprises culturing the seed culture in an aerobic condition of 15 to 35° C., and the culture is terminated at the point of time an absorbance of the spectrophotometer at a wavelength of 600 nm is 1.

9. The method according to claim 1,
wherein the step of preparing the fermentation product comprises fermenting the pre-culture for 1 to 10 days at 15 to 35° C.

\* \* \* \* \*